United States Patent
Tirendi et al.

(10) Patent No.: US 10,631,723 B1
(45) Date of Patent: Apr. 28, 2020

(54) SUBJECTIVE VISUAL ASSESSMENT SYSTEM AND METHOD

(71) Applicants: Richard S. Tirendi, Phoenix, AZ (US); James W. O'Neil, Phoenix, AZ (US)

(72) Inventors: Richard S. Tirendi, Phoenix, AZ (US); James W. O'Neil, Phoenix, AZ (US)

(*) Notice: Subject to any disclaimer, the term of this patent is extended or adjusted under 35 U.S.C. 154(b) by 27 days.

(21) Appl. No.: 15/966,627

(22) Filed: Apr. 30, 2018

Related U.S. Application Data

(60) Provisional application No. 62/500,404, filed on May 2, 2017.

(51) Int. Cl.
| | |
|---|---|
| *A61B 3/032* | (2006.01) |
| *G06T 1/00* | (2006.01) |
| *A61B 3/00* | (2006.01) |
| *G06T 3/00* | (2006.01) |
| *G16H 50/20* | (2018.01) |

(52) U.S. Cl.
CPC ............ *A61B 3/032* (2013.01); *A61B 3/0041* (2013.01); *G06T 1/0007* (2013.01); *G06T 3/0006* (2013.01); *G16H 50/20* (2018.01)

(58) Field of Classification Search
CPC ..... A61B 3/032; A61B 3/0025; A61B 3/0033; A61B 3/0041; A61B 3/0091
USPC ........................................................ 351/239
See application file for complete search history.

(56) References Cited

U.S. PATENT DOCUMENTS

| | | | |
|---|---|---|---|
| 9,517,008 B1* | 12/2016 | Berme | A61H 5/00 |
| 2012/0075586 A1* | 3/2012 | Kirschen | A61B 3/028 |
| | | | 351/239 |
| 2018/0101721 A1* | 4/2018 | Nienhouse | G06K 9/00288 |
| 2019/0216381 A1* | 7/2019 | Benford | A61B 5/162 |

* cited by examiner

*Primary Examiner* — Mohammed A Hasan
(74) *Attorney, Agent, or Firm* — Cahill Law Group LLC

(57) ABSTRACT

An automated visual performance assessment system and method includes a Smart Phone or similar device having a display to facilitate the presentation of objects for vision performance assessment conducted at a variety of distances between the cell phone and the subject as measured by the device. The device obtains measurement of the distance from the device to the subject under test and adjusts the sizing of objects to be displayed on the display based on the protocol being implemented for the test and assessment. The objects to be displayed will be selected and size modified to present the displayed object of appropriate size for the measured distance.

13 Claims, 2 Drawing Sheets

SUBJECTIVE VISUAL ASSESSMENT SYSTEM AND METHOD

RELATED APPLICATIONS

This application is related to and claims priority to a provisional application entitled "COMPUTERIZED VISION ASSESSMENT TECHNOLOGY BACKGROUND" filed May 2, 2017, and assigned Ser. No. 62/500,404.

FIELD OF THE INVENTION

The present invention is directed to visual assessment systems and methods and particularly to a subjective assessment system and method utilizing a fully automated mobile visual activity system incorporating automatic distance measurement and dynamic sizing of displayed test objects.

BACKGROUND OF THE INVENTION

Subjective vision screening or vision performance assessment is typically 20 performed with an eye chart that is situated a specific distance from the subject being tested. While standardized testing usually refers to the performance predicated on a twenty foot distance, professional offices seldom have the required dimensions to place an eye chart twenty feet from the subject; therefore, the objects or letters on the eye chart are sized in accordance with available test 25 distances. These distances are typically predetermined and are measured at the time of installation of the testing equipment. Eye charts are available that are calibrated for different testing distances that provide flexibility to the administrator of the test to utilize the physical parameters of the location of the test. The subject is then asked to identify the object on the chart and inform the administrator of that identification. The administrator notes the response from the subject and indicates in the record whether or not their response was correct or incorrect. Alternatively, the subject is requested to identify the smallest objects on the chart that the subject can correctly observe. The information derived from such tests are then available for evaluation. The assessment of visual acuity may require the test to be determined at two different distances. The distance may then be changed and the test repeated, or the chart is replaced with a chart displaying objects with the corrected size. Such dual test requirement is useful for the early detection of myopia, and is useful for developing treatment to slow the progression or worsening of the myopia condition over time. The procedures followed in present techniques for visual performance assessment include the measurement of the distance between the subject and the eye chart or objects to be viewed by the subject. The objects are predetermined of a particular size predicated on the distance available for the test in the facility in which the assessment is being performed. The object size is fixed and is associated with a specific distance so that the assessment is accomplished utilizing applicable testing protocols.

SUMMARY OF THE INVENTION

An automated visual performance assessment system and method is provided utilizing a smart phone, or similar electronic device having a display to facilitate vision performance assessment at a variety of test distances measured by the device. The tests at various distances can be conducted either dynamically in a single session or serially over time, each test incorporating the interaction of automated test distance measurements by the device and accompanying compensatory auto-adjustment of display sizing calibration based on the automated test distant measurement, and automated test protocol which may vary at the various distances and may also vary in accordance with the specific requirements for the subject under test. The testing protocol may vary at the various distances and provide automated result analysis at those various test distances. The result of the testing procedure provides outcome reporting based on the various test distances measured, with the retention of the data. The method of the invention incorporating the automated visual performance assessment permits analysis for differences in individual visual performance at the variety of test distances, monitoring of the visual performance changes over time, and permitting interaction with healthcare professionals for the purpose of initiating medical or educational treatment based on testing results.

BRIEF DESCRIPTION OF THE DRAWINGS

The present invention may more readily be described by reference to the accompanying drawings in which.

DETAILED DESCRIPTION OF THE INVENTION

Figure 1:
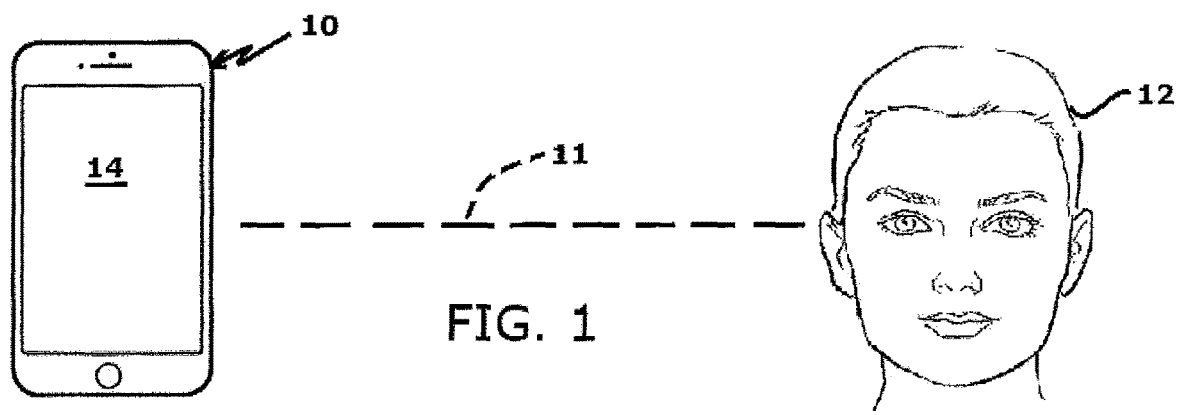
FIG. 1 is an illustration of the positioning of a Smart Phone, or similar electronic device, at a predetermined distance from a subject whose visual performance assessment is being undertaken. The Smart Phone or similar device provides a display for exhibiting appropriate protocol-chosen objects for the visual assessment.
Figure 2:
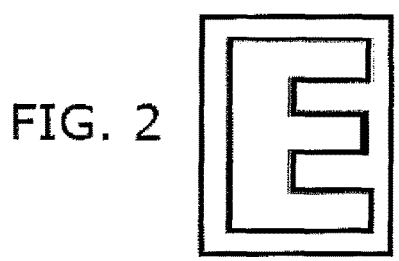
FIG. 2 is an illustration of a typical Snellen "E" that may be utilized in the visual performance assessment method of the present invention.

Referring to FIG. 1, a Smart Phone 10 or similar electronic device is illustrated positioned at a predetermined distance 11 from a test subject 12 whose visual performance assessment is to be undertaken. The electronic device may be a presently available cell phone or tablet having a display 14 for observation by the 25 subject. The objects to be displayed are determined by the selection of an appropriate protocol for presentation to a test subject; the objects to be displayed may be letters, forms, or other objects such as those conforming to Snellen parameters. For example, a Snellen "E" may be displayed as illustrated in FIG. 2; similarly, the size of the "E" will vary in accordance with the distance measured by the device between the device and the test subject. As the distance decreases, the device controls the size of the displayed object such as the reduced "E" shown in FIG. 3. The device is also provided with a distance measuring app that may take several forms and utilize different techniques for auto-ranging or predetermining the distance 11 from the device to the subject. The size of the displayed objects is adjusted to comport with the protocol required size determination for the object predicated upon the measured distance from the device to the subject. During the visual performance assessment, input is received from the subject in accordance with protocol requirements to identify the displayed object or perhaps to indicate the direction of a displayed object. A determination is made concerning the "correctness" of the test subject's input or identification of the displayed objects. Whether the response from the subject is "correct" or "incorrect" is a determination usually made by the administrator. This information is supplied to the device through any of several input means such as a touch screen input by the administrator, or a vocal/audio reception from the subject or a programmable reception of a visual indication from the subject. Various distance measuring or auto-ranging techniques may be employed, all of which are readily available in the form of apps incorporated or downloadable into the device. Such auto-ranging techniques include measurement of interpupilary distance of the subject, placing an object of known dimension on or with the subject, utilization of a low-powered transmitter such as Bluetooth or perhaps the utilization of the devices internal accelerometers typically available for use in Smart Phones.

Figure 3:
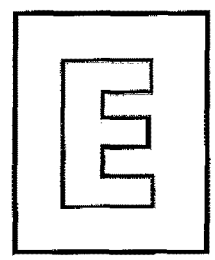
FIG. 3 is an illustration of the display presentation of the Snellen "E" of FIG. 2 wherein the letter size has been reduced in accordance with the distance measuring or auto-ranging implemented in the method and system of the present invention.

The distance measurement or auto-range is determined at the time the test is given and the visual performance assessment is undertaken. If the protocol requires that the test be performed at more than a single distance, the position of the electronic device can be moved to accomplish successive portions of the test. as indicated above, FIGS. 2 and 3 are illustrations of a typical Snellen object comprising the letter "E" indicating that the size of the letter being displayed on the device in FIG. 2 is reduced to the size shown in FIG. 3 in accordance with the lessening of the distance from the device to the subject. The size of the object being displayed determined by the appropriate protocol in combination with the distance measured contemporaneously with the assessment procedure.

Figure 4:
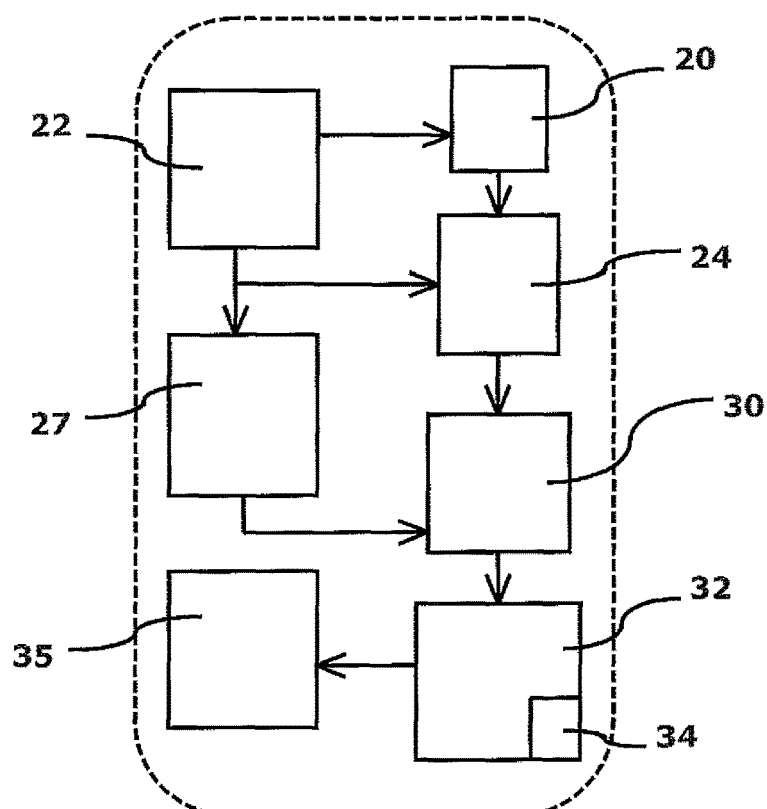
FIG. 4 is a functional block diagram illustrating the components of the Smart Phone or tablet or similar electronic device utilized in the administration of the automated visual performance assessment method.

An embodiment of the present invention is illustrated in FIG. 4 in the form of a functional block diagram illustrating the components of the Smart Phone or tablet or similar electronic device utilized in the administration of the automated visual performance assessment method. Subject data is entered 20 into the device such as name, age, gender and any relevant medical or historical information that may be necessary to appropriately identify the proper protocol for the test to be administered. This information is applied to data storage memory 22. In those instances where the subject has previously been tested utilizing the system of the present invention, the data memory storage may have the historical data relevant to the subject. This information, both entered and stored is then utilized to determine and select the appropriate protocol 24 for the forthcoming test or performance assessment. The selected protocol will determine the selection of images, the sequence of presentation, and in some instances the timing of the presentation to be presented to the subject. This presentation information is then modified by determining image size predicated on the distance measuring or auto-ranging system 27 of the device.

Those skilled in the art will appreciate the availability of various apps and available features of typical cell phone technology for determining distance between the device and the test subject. The preferred embodiment utilizes the subject's interpupilary distance as the basis for determining distance from the subject to the device. The distance between the subject's pupils can be measured at the time of the visual performance assessment such as by measuring, by ruler or otherwise, the distance between the pupils. In those instances where the history of the subject is already stored in the device, the interpupilary distance would be one of the factors saved in memory and thus automatically accessible when the memory is accessed for purposes of conducting the evaluation. Knowing the distance between the subject's pupils, the cell phone camera and imaging sensor and readily available software can subsequently identify the pattern recognition of the subject's pupils, count the number of pixels separating the pupils, and compute the distance from the pupils to the camera lens. The technique of utilizing a known object size as a basis for determining distance from a cell phone or similar electronic device and an observed object or subject is well known to those skilled in the art. A similar technique may be utilized by placing an object or "target" on the subject with known fixed dimensions. The same technique utilized and described above in regard to interpupilary distance is then utilized to determine device-subject distance. The technique is identical to that used when measuring the subject's interpupilary distance but the target is replaced by substituting the object of known dimension (for example, a scale or diagram with known specific dimensions).

Other distance measuring techniques may be implemented such as by providing a low powered transmitter (Bluetooth protocol) that has been calibrated at a known distance. The transmission strength as it is detected at the device may then be utilized to estimate distance from the subject and transmitted to the device. It may also be possible to utilize the device's internal accelerometer, accelerometers are inherent in most mobile devices such as cell phones that utilize the motion and acceleration of the device to determine length of any chosen movement. That is, the device can be placed at the subject's location and then activate the accelerometer feature of the device which then measures the subsequent movement of the mobile device from the subject to the test's testing distance dictated by the required protocol. There are other techniques including available apps for utilization with cell phones to determine distance from an observed object and the cell phone; any of the distance measuring devices would be appropriate as an element to the system of the present invention and the method of the invention wherein the visual performance assessment provides a displayed object of proper size and orientation dictated by the measurement achieved by the cell phone or similar device. The system and method of the present invention therefore provides a "dynamic real time" image size determination 30 or size modification of displayed objects predicated on the distance between the device and the test subject as determined by the distance measuring or auto-ranging of the device.

Image size modification predicated on contemporaneously measured distance may be accomplished in numerous ways. A preferred embodiment would be the utilization of a "lookup table". Information in the form of signals derived from the distance measurement system of the device can be applied to the table and the selection of object or optotype selected by the protocol may be modified as a result of the table contents. Every optotype, whether it is a letter, number, or shape has a defined height, width and stroke width as a function of the viewing distance and the Snellen value. For example, optotypes from the HOTV Chart of size 20/100 are defined to have a height of 0.698 inches at a distance of eight feet. Similarly, that same optotype of size 20/50 is defined to be 0.349 inches at a distance of eight feet. The same optotype of size 20/100 is defined to be 1.396 inches at a distance of sixteen feet. The ratio of image height to image width and image stroke width of optotypes are fixed and defined by the artwork or prescribed graphical definition of the optotype itself. Therefore, the proposed lookup table of calibrated values need only contain the height for each unique optotype family of a known size. The system may then display the selected object in a size indicated by the lookup table for that distance. Other techniques may be used to modify or alter the size of a displayed object including a mathematical modification of stored object dimensions. It may be noted however, that no aspect ratios are modified during any size modification to thus maintain proper image presentation on the display of the device.

If the protocol specifically requires a predetermined distance, with no alternative distance, the distance measuring or auto-ranging system may prevent or abort the administration of the performance assessment of the measured distance is incorrect and indicate that the distance being utilized for the specific test is improper. The image size thus produced as a result of the selected image from the protocol and the modification of the image size by the distance measuring or auto-arranging system of the device results in the presentation of a display presented to the subject. The display 32 may incorporate chosen Snellen objects of the appropriate size for the distance at which the performance assessment is taking place.

Since the method is a subjective performance assessment, input from the subject is required to indicate the identification of the image, or perhaps the orientation of the image, in accordance with the selected or required protocol. The response from the subject may be "correct" or "incorrect". That is, if the subject is observing a displayed Snellen "E" for example, and the subject misidentifies the letter, that correctness evaluation, or information of incorrectness of the observation is entered into the system; this system entrance may be as a result of administrator input such as by a touch screen input 34. Alternatively, this feedback input from the subject may be accomplished for example by a voice recognition software attuned to the subject's speech characteristics such that the utterance or the pronunciation of the displayed letter may be identified as a result of the subject vocalizing the identification of the display object. The "correctness" of the identification is then determined by speech recognition software.

The results of the visual performance assessment is stored in the test results memory 35; the results memory may be utilized as a feedback to the input data storage 22 to be added to the data associated with the subject's name and also may be utilized to be transmitted to remote memory locations.

Figure 5:
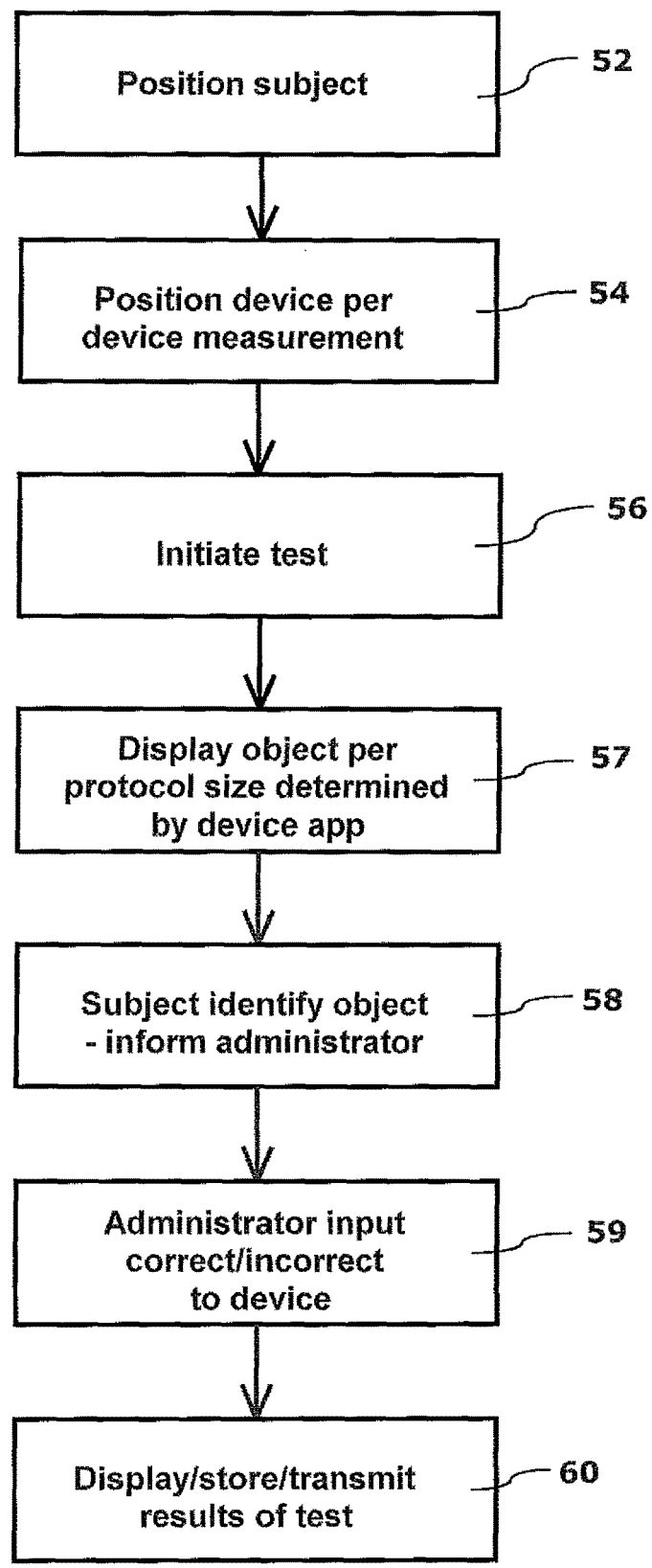
FIG. 5 is a flow diagram illustrating the method of the present invention.

The method of the present invention is generally illustrated by the flow diagram of FIG. 5. The subject to be tested is appropriately positioned 52; the subject may be placed in a fixed standing position or in a sitting position. The subject's data file will dictate the appropriate protocol to be utilized for the test which will include the designated distance at which the test is to be performed. The administrator will then move with the device to the appropriate distance dictated by the protocol 54. The device will provide an indication of the distance to guide the administrator to the proper administrator position. The administrator initiates the start of the test 56. The visual performance assessment then proceeds with the display 57 of an appropriate object; the precise scale or size of the object being displayed is controlled by the measured distance obtained by the device. The subject informs the administrator what they see on the device. The subject identifies the objects 58 being viewed and informs the administrator; for example, he may state to the administrator that he sees letters "H", "O" and "V". Similarly, the subject may state to the administrator that he "sees a circle, square, and a triangle". The administrator provides an input 59 to the device concerning the answers that he received from the subject in response to the objects being displayed on the device. This evaluation input from the administrator indicates whether or not the subject correctly or incorrectly identified the objects being displayed; this information may be entered into the device via touch screen activated by the administrator. The protocol being utilized for this assessment may respond to the results of the test to indicate additional evaluation procedures including a variation in the testing distance or perhaps the occlusion of the eyes or the selection a different optotype family. The test may then continue at the instructions of the protocol. Upon completion of the test, the administrator is provided with the results onscreen 60 including the ability to print, email, text or transmit the test results to local memory or to remote memory locations for storage, further evaluation, or reference to further testing activity.

The method of the present invention may also be utilized in other's screening or vision performance assessments such as the measurement of convergence insufficiency. The measurement of convergence insufficiency is a disorder which results in eye misalignment at near distances and can impact reading ability. The detection of this disorder is particularly important in relation to school age children wherein such disorder could significantly affect learning ability and performance. Utilizing the present invention, the protocol for administration of the test is again either provided to the device or is already stored in the device in the data storage memory of the device. Access to the stored data may be accomplished by providing the subject's name and other identifying information to the device. The subject under test is positioned, and the administrator, in accordance with the stored protocol, provides an image on the device screen. The device is placed near the patient and slowly moved closer to the subject until the object "breaks" into two images. The distance indicated by the device at this point is noted; the test may be repeated several times to verify the readings obtained through the test; the value of this distance may be compared to the "near point of convergence" values to normal values for the age of the subject. The size of the object being displayed may or may not be modified and will depend on the requirements of the protocol. This "near point of convergence", sometimes referred to as "break point" is often a range of values wherein the test object begins to separate the objects being viewed but can bring those objects back together with additional focusing effort, but then eventually breaks into two objects and remains a double vision even at closer distances. The image, dictated by the protocol may be a familiar test image or simply a single spot or point of light.

The test continues by determining the "recovery distance" wherein the device is slowly moved from the position wherein the image breaks into two images slowly further away from the subject until the double vision comes back together and the object being viewed is again perceived as a single object. This recovery distance is also automatically measured by the device; the distance of the "break point" and the recovery distance are therefore each automatically measured by the device and are noted and stored in the device through an input from the administrator. The input may take the form of a simple touch screen input on the device in response to communication from the subject to the administrator of the corresponding event.

The system and method may also be utilized for the investigation of the condition known as presbyopia. The device, pursuant to the directions of a protocol stored in the device, will present an object on the screen to the subject. The device is brought closer and closer to the subject until the displayed object becomes too blurred to the subject to read. The distance measured by the device is then noted; the image is then moved further away until the object is once again clear. This distance is also noted. The distances are thus determined by the communication by the subject to the administrator who provides an input to the device (such as by touch screen) wherein the distance measured at that moment is stored in the device. The size of the object being displayed may be adjusted to maintain a constant visual angle on the retina—any displayed object size change is determined by the protocol for that test and is controlled by the distance measurement app in the device.

The system and method of the present invention is also applicable to an improved technique for the determination and measurement of myopia. Prior art techniques include the assessment and comparison of visual acuity measurements at two different distances (near and far). The present invention permits the visual acuity assessment to occur dynamically as the vision testing distances become progressively more remote. A projected image that may be a 20/20 line is presented to the subject; as the object becomes more remote, the object blurs to the subject. An automatic adjustment of calibration of the object based on automatic assessment of testing distance would allow dynamic adjustments to keep the 20/20 line that has been selected in perfect calibration as the testing distance becomes more remote. The remote distance at which the line remained in clear focus would be the focal point of the eye and this distance would allow a calculation of myopia (Diopters). Utilization of the invention is therefore quicker and more accurate system for monitoring the presence of or changes nearsightedness.

The present invention has been described in terms of selected specific embodiments of the apparatus and method incorporating details to facilitate the understanding of the principles of construction and operation of the invention. Such reference herein to a specific embodiment and details thereof is not intended to limit the scope of the claims appended hereto. It will be apparent to those skilled in the art that modifications may be made in the embodiments chosen for illustration without departing from the spirit and scope of the invention.

What is claimed:

1. An automated visual performance assessment test method using an electronic device having a memory, a camera for viewing a test subject, a visual display for displaying a test object to the test subject, and a distance measuring app in the device for automatically measuring the distance between the device and the test subject comprising:
   (a) positioning a subject to be tested;
   (b) moving the device a measured distance from the test subject dictated by a test protocol in the device, the distance measured by the distance measuring app in the device;
   (c) initiating the test;
   (d) displaying an object dictated by the protocol in the memory of the device on the display of the device, the size of the object determined by the distance measured by the device;
   (e) receive in the device identification of the objects by the subject viewed on the display;
   (f) determine the correctness of the identification to produce a correctness evaluation;
   (g) entering the correctness evaluation into the device indicating the correctness of information received from the subject; and
   (h) displaying the results of the test on the display to permit the storage of the test results in local memory, the transmission of the test results to remote memory locations for storage, further evaluation, or reference to further testing activity.

2. An automated visual performance assessment test method using an electronic device having a memory, a camera for viewing a test subject, a visual display for displaying a test object to the test subject, and a distance measuring app in the device for automatically measuring the distance between the device and the test subject comprising:
   (a) positioning a subject to be tested;
   (b) moving the device a measured distance from the test subject dictated by a test protocol in the device, the distance measured by the distance measuring app in the device;
   (c) initiating the test;
   (d) displaying an object dictated by the protocol in the memory of the device on the display of the device, the size of the object determined by the distance measured by the device;
   (e) receive in the device identification of the objects by the subject viewed on the display;
   (f) determine the correctness of the identification to produce a correctness evaluation;
   (g) entering the correctness evaluation into the device indicating the correctness of information received from the subject; and
   (h) displaying the results of the test on the display to permit the storage of the test results in local memory, the transmission of the test results to remote memory locations for storage, further evaluation, or reference to further testing activity;
   (i) moving the device to a different distance dictated by the test protocol in the device and measuring the different distance by the distance measuring app in the device, and repeating steps (a) through (h).

3. An automated visual performance assessment test method using an electronic device having a memory, a camera for viewing a test subject, a visual display for displaying a test object to the test subject, and a distance measuring app in the device for automatically measuring the distance between the device and the test subject comprising:
   (a) positioning a subject to be tested;
   (b) displaying an object dictated by a protocol in the memory of the device on the display to be viewed by the test subject;
   (c) moving the device slowly toward the test subject until a break point is reached where the test object becomes unrecognizably blurred, too small to be resolved, or splits into two as communicated by the test subject to a test administrator;
   (d) storing in the device the distance at which the break point is reached; and
   (e) slowly moving the device away from the test subject until the test object becomes recognizable or becomes one object to establish a recovery distance and storing in the device the recovery distance measured by the device.

4. An automated visual performance assessment test method using an electronic device having a memory, a camera for viewing a test subject, a visual display for displaying a test object to the test subject, and a distance measuring app in the device for automatically measuring the distance between the device and the test subject comprising:

(a) positioning a subject to be tested;
(b) displaying an object dictated by a protocol in the memory of the device on the display to be viewed by the test subject;
(c) positioning the device with respect to the subject to insure that the object being viewed at a distance that permits the test subject to view the object in clear focus;
(d) moving the device slowly away from the test subject until the object becomes blurred to the test subject;
(e) adjusting the size of the displayed object as the distance from the test subject increases to maintain the correct size/distance dictated by the protocol; and
(f) storing in the device the distance at which the displayed object becomes blurred to the test subject and storing results of the test in memory.

5. An automated visual performance test system for assessing the visual performance of a test subject comprising:
  (a) an electronic device having a camera for viewing a test subject;
  (b) a visual display on the device for displaying a test object to the test subject;
  (c) a distance measuring app in the device for automatically measuring the distance between the device and the test subject; and
  (d) the size of the object on the device visual display being displayed to the test subject adjusted by the device based on the automatic measurement by the device of the distance between the device and the test subject.

6. The automated visual performance test system of claim 5 wherein said electronic device is a cell phone.

7. The automated visual performance test system of claim 5 wherein said electronic device is a tablet.

8. An automated visual performance test system for assessing the visual performance of a test subject comprising:
  (a) an electronic device having a camera for viewing a test subject;
  (b) a visual display on the device for displaying a test object to the test subject;
  (c) a distance measuring app in the device for automatically measuring the distance between the device and the test subject wherein said distance measuring app measures the distance between the device and the test subject based on the interpupilary distance of the test subject; and
  (d) the size of the object on the device visual display being displayed to the test subject is adjusted by the device based on the automatic measurement by the device of the distance between the device and the test subject.

9. The automated visual performance test system for assessing the visual performance of a test subject of claim 8 wherein said device is a cell phone.

10. The automated visual performance test system for assessing the visual performance of a test subject of claim 8 wherein said device is a tablet.

11. An automated visual performance test system for assessing the visual performance of a test subject comprising:
  an electronic device having
  (a) a camera for viewing a test subject;
  (b) a visual display for displaying a test object to the test subject;
  (c) a distance measuring app for automatically measuring the distance between the device and the test subject;
  (d) a test protocol memory for storing test protocols each protocol including objects to be displayed on said display during a test; and
  (e) means in said device connected to said distance measuring app for adjusting image size of the displayed object in accordance with requirements of a stored protocol;
wherein the size of objects displayed on the device visual display is determined by the protocol and the distance measuring app.

12. The automated visual performance test system for assessing the visual performance of a test subject of claim 11 wherein said device is a cell phone.

13. The automated visual performance test system for assessing the visual performance of a test subject of claim 11 wherein said device is a tablet.

* * * * *